(12) United States Patent
Goto et al.

(10) Patent No.: US 10,617,684 B2
(45) Date of Patent: Apr. 14, 2020

(54) AQUEOUS DRUG

(71) Applicant: KYORIN PHARMACEUTICAL CO., LTD., Tokyo (JP)

(72) Inventors: Takahiro Goto, Tochigi (JP); Hitoshi Kozuka, Tochigi (JP); Mizuho Shibata, Tochigi (JP)

(73) Assignee: KYORIN PHARMACEUTICAL CO., LTD., Tokyo (JP)

( * ) Notice: Subject to any disclaimer, the term of this patent is extended or adjusted under 35 U.S.C. 154(b) by 2 days.

(21) Appl. No.: 15/578,755

(22) PCT Filed: Jun. 2, 2016

(86) PCT No.: PCT/JP2016/066395
§ 371 (c)(1),
(2) Date: Dec. 1, 2017

(87) PCT Pub. No.: WO2016/195014
PCT Pub. Date: Dec. 8, 2016

(65) Prior Publication Data
US 2018/0153875 A1    Jun. 7, 2018

(30) Foreign Application Priority Data

Jun. 2, 2015    (JP) .................................. 2015-111862

(51) Int. Cl.
| | | |
|---|---|---|
| *A61K 31/4709* | (2006.01) | |
| *A61K 9/08* | (2006.01) | |
| *A61K 47/02* | (2006.01) | |
| *A61K 47/12* | (2006.01) | |
| *A61K 47/18* | (2017.01) | |

(52) U.S. Cl.
CPC ............ *A61K 31/4709* (2013.01); *A61K 9/08* (2013.01); *A61K 47/02* (2013.01); *A61K 47/12* (2013.01); *A61K 47/18* (2013.01); *A61K 47/183* (2013.01)

(58) Field of Classification Search
None
See application file for complete search history.

(56) References Cited

U.S. PATENT DOCUMENTS

| | | | |
|---|---|---|---|
| 4,722,733 A | * | 2/1988 | Howson |
| 5,304,559 A | | 4/1994 | Rozier |
| 5,334,589 A | | 8/1994 | Al-Razzak et al. |
| 5,811,130 A | | 9/1998 | Boettner et al. |
| 6,288,080 B1 | | 9/2001 | Barsuhn et al. |
| 10,206,917 B2 | | 2/2019 | Goto et al. |
| 2004/0082593 A1 | | 4/2004 | Sommermeyer et al. |
| 2006/0281779 A1 | | 12/2006 | Asahina et al. |
| 2007/0197548 A1 | | 8/2007 | Murthy |
| 2009/0117205 A1 | | 5/2009 | Yano et al. |
| 2014/0288310 A1 | | 9/2014 | Araya et al. |
| 2016/0067185 A1 | | 3/2016 | Uchida et al. |
| 2016/0074330 A1 | | 3/2016 | Uchida et al. |
| 2018/0147199 A1 | | 5/2018 | Minagawa et al. |

FOREIGN PATENT DOCUMENTS

| | | |
|---|---|---|
| EP | 3305295 | 4/2018 |
| EP | 3305296 | 4/2018 |
| JP | 63-188626 | 8/1988 |
| JP | 2-264724 | 10/1990 |
| JP | 4-230631 | 8/1992 |
| JP | 2003-226643 | 8/2003 |
| JP | 2004-509921 | 4/2004 |
| WO | 91/09525 | 7/1991 |
| WO | 97/23217 | 7/1997 |
| WO | 99/29322 | 6/1999 |
| WO | 2005/026147 | 3/2005 |
| WO | 2006/004028 | 1/2006 |
| WO | 2014/174846 | 10/2014 |
| WO | 2014/174847 | 10/2014 |
| WO | 2014/174848 | 10/2014 |

OTHER PUBLICATIONS

"Tromethamine", National Center for Biotechnology Information, PubChem Compound Database; CID=6503, downloaded from "https://pubchem.ncbi.nlm.nih.gov/compound/6503" on Feb. 3, 2019, 2 pages.*
International Preliminary Report on Patentability dated Dec. 5, 2017 in International (PCT) Application No. PCT/JP2016/066395.
International Search Report dated Jul. 12, 2016 in International (PCT) Application No. PCT/JP2016/066395.
Extended European Search Report dated Jan. 18, 2019 in European Patent Application No. 16803448.6.

* cited by examiner

*Primary Examiner* — Savitha M Rao
*Assistant Examiner* — Gregg Polansky
(74) *Attorney, Agent, or Firm* — Wenderoth, Lind & Ponack, L.L.P.

(57) ABSTRACT

An aqueous drug in which the chemical decomposition of the compound represented by formula (1) or of a salt thereof is inhibited, and a method for producing said aqueous drug. An aqueous drug provided with: a solution (liquid A) that contains the compound represented by formula (1) or a salt thereof and that has a pH of 5.3 or less; and a dilution liquid (liquid B) that is mixed with the liquid A in order to prepare a solution to be administered.

10 Claims, 3 Drawing Sheets

| No. | 2θ | RELATIVE INTENSITY | INTENSITY |
|---|---|---|---|
| 1 | | | |
| 2 | 9.5 | m | 872 |
| 3 | | | |
| 4 | 11.6 | s | 2286 |
| 5 | | | |
| 6 | 13.3 | m | 825 |
| 7 | 14.4 | m | 1336 |
| 8 | 14.7 | s | 1913 |
| 9 | 15.7 | m | 778 |
| 10 | 15.8 | m | 940 |
| 11 | 16.4 | m | 945 |
| 12 | 16.9 | m | 772 |
| 13 | 17.1 | m | 717 |
| 14 | 17.3 | m | 1140 |
| 15 | | | |
| 16 | 18.5 | w | 485 |
| 17 | 19.2 | w | 310 |
| 18 | 19.5 | m | 525 |
| 19 | 19.7 | m | 610 |
| 20 | 19.9 | w | 302 |
| 21 | 20.2 | m | 718 |
| 22 | 21.2 | s | 1990 |
| 23 | 21.6 | m | 1335 |
| 24 | | | |
| 25 | 22.4 | m | 757 |
| 26 | 23.4 | m | 1393 |
| 27 | 23.9 | m | 552 |
| 28 | 24.2 | m | 855 |
| 29 | | | |
| 30 | 25.0 | m | 1088 |
| 31 | 25.3 | w | 470 |
| 32 | 25.5 | m | 695 |
| 33 | 25.8 | m | 663 |
| 34 | 26.0 | m | 997 |
| 35 | | | |
| 36 | 26.8 | m | 1677 |
| 37 | 27.3 | m | 992 |
| 38 | 27.8 | m | 715 |
| 39 | 28.3 | m | 717 |
| 40 | 29.0 | w | 395 |
| 41 | 29.5 | m | 610 |
| 42 | 30.3 | w | 330 |
| 43 | 31.6 | m | 615 |
| 44 | 32.2 | m | 553 |
| 45 | 32.5 | w | 405 |
| 46 | 32.8 | m | 843 |
| 47 | 33.1 | w | 402 |
| 48 | 33.6 | m | 835 |
| 49 | 34.0 | w | 338 |
| 50 | 34.4 | w | 358 |
| 51 | 34.8 | m | 593 |
| 52 | 35.4 | m | 510 |
| 53 | 36.1 | w | 388 |
| 54 | 36.5 | w | 455 |
| 55 | 36.8 | w | 435 |
| 56 | 38.0 | m | 625 |
| 57 | 39.3 | w | 380 |

DEFINITION
% RELATIVE INTENSITY (rl)    DEFINITION
  50 ≤ rl ≤ 100               vs (VERY STRONG)
  20 ≤ rl < 50                s  (STRONG)
  5 ≤ rl < 20                 m (MODERATE)
  0.7 ≤ rl < 5                w (WEAK)
     rl < 0.7                 vw (VERY WEAK)

FIG.3

AQUEOUS DRUG

TECHNICAL FIELD

The present invention relates to an aqueous liquid formulation. More specifically, the present invention relates to an aqueous liquid formulation including a solution that contains a compound represented by general formula (1) (hereinafter, also referred to as a compound of formula (1)) or a salt thereof.

[Chemical Formula 1]

(1)

In the formula (1), $R^1$ represents an alkyl group having 1 to 3 carbon atoms which is optionally substituted with one or more substituents selected from the group consisting of a hydrogen atom, a halogen atom, an amino group, a cyano group, or a hydroxyl group, $R^2$ represents a hydrogen atom, a halogen atom, a hydroxyl group, an amino group or an alkyl group having 1 to 3 carbon atoms which is optionally substituted with one or more substituents selected from the group consisting of a hydrogen atom, a halogen atom, an amino group, a cyano group or a hydroxyl group, $R^3$ represents a hydrogen atom or a halogen atom, $R^4$ represents a hydrogen atom or a halogen atom, and X represents a halogen atom.

BACKGROUND ART

It is known that a 7-[4-substituted-3-{(cyclopropylamino) methyl}-1-pyrrolidinyl]q uinolone carboxylic acid derivative not only is safe and has a strong antibacterial activity, but also exhibits a strong antibacterial activity to resistant bacteria such as methicillin-resistant *Staphylococcus aureus* (MRSA), penicillin-resistant *Streptococcus pneumoniae* (PRSP), and vancomycin-resistant *Enterococcus* (VRE) (Patent Literature 1).

An aqueous liquid formulation having a pH that is higher or lower than the physiological pH sometimes provides stimuli when administered. Hence, it is preferable to design an aqueous liquid formulation which has a pH around the physiological pH, that is, a near-neutral pH, when designing an aqueous liquid formulation such as an injectable formulation. Patent Literatures 2 to 7 disclose an aqueous liquid formulation in which a quinolone carboxylic acid derivative is contained as a principal agent and which is neutral pH. These literatures disclose a formulation in which the precipitation of the principal agent is suppressed and the principal agent is solubilized by adding polyvalent metal such as magnesium into a solution (Patent Literatures 2 to 7). Examples of the formulation form include an injectable formulation (Patent Literatures 2 to 5 or 7) and an ophthalmic formulation (Patent Literatures 5 to 7). In any formulation, the principal agent and the polyvalent metal are simultaneously contained in the solution or the suspension, thereby to suppress the precipitation of the principal agent and exert the solubilization effect.

On the other hand, there is known an aqueous liquid formulation in which a solution containing a quinolone carboxylic acid derivative as a principal agent is adjusted to be slightly acidic around pH 4 thereby to improve the chemical and physical stability of the principal agent (Patent Literatures 8 to 9). Patent Literature 9 discloses a formulation which includes a lyophilized formulation containing quinolone carboxylic acid and a dilution liquid containing a polyvalent metal compound.

It is noted that the above-described quinolone carboxylic acid derivative disclosed in Patent Literatures 2 to 9 does not have a cyclopropylaminomethyl structure.

CITATION LIST

Patent Literature

Patent Literature 1: WO2005/026147
Patent Literature 2: WO1991/009525
Patent Literature 3: WO1997/023217
Patent Literature 4: WO1999/29322
Patent Literature 5: JP1988-188626
Patent Literature 6: JP1992-230631
Patent Literature 7: JP1990-264724
Patent Literature 8: JP2004-509921
Patent Literature 9: WO2006/004028

SUMMARY OF INVENTION

Technical Problem

An object of the present invention is to provide a novel aqueous liquid formulation that contains a compound of formula (1) or a salt thereof, in which the chemical decomposition of the compound of the formula (1) or a salt thereof is inhibited.

Solution to Problem

The present inventors intensively conducted research on the preparation of the aqueous liquid formulation that contains the compound of the formula (1) or a salt thereof. As a result, they determined that the cyclopropylaminomethyl structure contained in the compound of the formula (1) is likely to be chemically decomposed, causing the generation of a compound represented by general formula (2) (hereinafter, also referred to as a "compound of formula (2)") in which a cyclopropyl group is detached:

[Chemical Formula 2]

(2)

(wherein, $R^1$, $R^2$, $R^3$ and X are defined as described above). The present invention provides a novel aqueous liquid formulation and a production method thereof, in which the generation of the compound of the formula (2) is inhibited even when the compound of the formula (1) or a salt thereof, for which the formulation is difficult to produce as described above, is contained.

The present inventors have found that the generation of the compound of the formula (2) is inhibited when the aqueous liquid formulation is provided with an acidic solution that contains the compound of the formula (1) or a salt thereof, and completed the present invention.

The present invention will be described in further detail below.

<1> An aqueous liquid formulation including:
(liquid A): a solution that contains a compound represented by general formula (1):

[Chemical Formula 3]

(1)

(wherein $R^1$ represents an alkyl group having 1 to 3 carbon atoms which is optionally substituted with one or more substituents selected from the group consisting of a hydrogen atom, a halogen atom, an amino group, a cyano group, or a hydroxyl group, $R^2$ represents a hydrogen atom, a halogen atom, a hydroxyl group, an amino group or an alkyl group having 1 to 3 carbon atoms which is optionally substituted with one or more substituents selected from the group consisting of a hydrogen atom, a halogen atom, an amino group, a cyano group or a hydroxyl group, $R^3$ represents a hydrogen atom or a halogen atom, $R^4$ represents a hydrogen atom or a halogen atom, and X represents a halogen atom.) or a salt thereof and that has a pH of 5.3 or less; and (liquid B): a dilution liquid that is mixed with the liquid A to prepare a solution for administration.

<2> The aqueous liquid formulation according to <1>, wherein the liquid A and the liquid B are mixed to preprare the solution for administration having a pH of 6.3 or more.

<3> The aqueous liquid formulation according to <1> or <2>, wherein the liquid B contains a magnesium compound, and the molar ratio of the magnesium compound relative to the compound represented by the formula (1) or a salt thereof is 0.6 or less.

<4> The aqueous liquid formulation according to any one of <1> to <3>, wherein the magnesium compound is not contained in the liquid A.

<5> The aqueous liquid formulation according to any one of <1> to <4>, wherein the liquid B further contains a buffer.

<6> The aqueous liquid formulation according to <5>, wherein the buffer is sodium hydrogen carbonate, trometamol, a phosphoric salt, glycine, meglumine, citric acid, or a citric salt.

<7> The aqueous liquid formulation according to <5> or <6>, wherein the buffer is sodium hydrogen carbonate, trometamol, or glycine.

<8> The aqueous liquid formulation according to any one of <1> to <7>, wherein the concentration of the compound represented by the formula (1) in the liquid A is 1.5 mg/mL or more and 8 mg/mL or less.

<9> The aqueous liquid formulation according to any one of <1> to <8>, wherein the liquid A and the liquid B are housed in separate housing units, and are to be mixed by making the housing units of the liquid A and the liquid B communicate with each other when administered.

<10> The aqueous liquid formulation according to <9>, wherein the housing unit of the liquid A and the housing unit of the liquid B are constituted by separate containers, respectively.

<11> An aqueous liquid formulation including a compound represented by general formula (1):

[Chemical Formula 4]

(1)

(wherein $R^1$ represents an alkyl group having 1 to 3 carbon atoms which is optionally substituted with one or more substituents selected from the group consisting of a hydrogen atom, a halogen atom, an amino group, a cyano group, or a hydroxyl group, $R^2$ represents a hydrogen atom, a halogen atom, a hydroxyl group, an amino group or an alkyl group having 1 to 3 carbon atoms which is optionally substituted with one or more substituents selected from the group consisting of a hydrogen atom, a halogen atom, an amino group, a cyano group or a hydroxyl group, $R^3$ represents a hydrogen atom or a halogen atom, $R^4$ represents a hydrogen atom or a halogen atom, and X represents a halogen atom) or a salt thereof and having a pH of 5.3 or less.

<12> An aqueous liquid formulation including
(liquid A): a solution that contains a compound represented by general formula (1):

[Chemical Formula 5]

(1)

(wherein R¹ represents an alkyl group having 1 to 3 carbon atoms which is optionally substituted with one or more substituents selected from the group consisting of a hydrogen atom, a halogen atom, an amino group, a cyano group, or a hydroxyl group, R² represents a hydrogen atom, a halogen atom, a hydroxyl group, an amino group or an alkyl group having 1 to 3 carbon atoms which is optionally substituted with one or more substituents selected from the group consisting of a hydrogen atom, a halogen atom, an amino group, a cyano group or a hydroxyl group, R³ represents a hydrogen atom or a halogen atom, R⁴ represents a hydrogen atom or a halogen atom, and X represents a halogen atom) or a salt thereof and that has a pH of 5.3 or less, and (liquid B): a solution that contains trometamol or glycine, and a magnesium compound and that has a pH of 8.0 or more and 10.0 or less, wherein the liquid A and the liquid B are mixed to prepare a solution for administration.

Advantageous Effects of Invention

According to the present invention, the novel aqueous liquid formulation that contains the compound of the formula (1) or a salt thereof, in which the chemical decomposition of the compound of the formula (1) is suppressed, can be provided.

DESCRIPTION OF EMBODIMENTS

An aqueous liquid formulation according to the present embodiment contains a liquid A and a liquid B. The liquid A and the liquid B are mixed to prepare a solution for administration. The solution for administration is administered to a subject. The liquid A is a solution that contains a compound represented by the formula (1) below or a salt thereof and that has a pH of 5.3 or less. Also, the liquid B is a dilution liquid for diluting the liquid A.

[Chemical Formula 6]

(1)

In the formula (1), R¹ represents an alkyl group having 1 to 3 carbon atoms which is optionally substituted with one or more substituents selected from the group consisting of a hydrogen atom, a halogen atom, an amino group, a cyano group, or a hydroxyl group, R² represents a hydrogen atom, a halogen atom, a hydroxyl group, an amino group or an alkyl group having 1 to 3 carbon atoms which is optionally substituted with one or more substituents selected from the group consisting of a hydrogen atom, a halogen atom, an amino group, a cyano group or a hydroxyl group, R³ represents a hydrogen atom or a halogen atom, R⁴ represents a hydrogen atom or a halogen atom, and X represents a halogen atom.

As described herein, the liquid A is a liquid mixture in a state in which the compound of the formula (1) or a salt thereof is dissolved in a physiologically acceptable carrier. The liquid A is a solution of the compound of the formula (1) or a salt thereof, in which the compound of the formula (1) or a salt thereof is dissolved in a physiologically acceptable carrier.

The "physiologically acceptable carrier" described herein is any solvent or solution which is not harmful when the carrier is administered to a patient. Also, as described herein, the solution refers to a liquid mixture in a state in which a solute is dissolved in a solvent.

Examples of the physiologically acceptable carrier may include water, a saline solution, a Ringer's solution, a glucose solution, a lactate Ringer's solution, an acetate Ringer's solution, a bicarbonate Ringer's solution, a maltose liquid, and a xylitol liquid. For example, the physiologically acceptable carrier may be include one or more thereof. As the physiologically acceptable carrier according to the present embodiment, water may be particularly preferable.

The "aqueous liquid formulation" described herein is a formulation that contains water as base material and is in the form of liquid. Examples thereof may include an injectable formulation, an ophthalmic liquid drug, aqueous nasal drops, aqueous ear drops, and an inhalant liquid drug.

The "injectable formulation" described herein is a sterile formulation to be directly administered to body tissues and organs, such as subcutaneous or intramuscular tissues and blood vessels.

The "halogen atom" described herein represents a fluorine atom, a chlorine atom, a bromine atom, or an iodine atom. Among these, a fluorine atom is preferable. The "alkyl group having 1 to 3 carbon atoms" described herein represents a methyl group, an ethyl group, a propyl group, or a 2-propyl group. The compound of the formula (1) to be contained in the aqueous liquid formulation according to the present embodiment may be preferably 7-[3-{(cyclopropylamino) methyl}-4-fluoropyrrolidine-1-yl]-6-fl uoro-1-(2-fluoro-ethyl)-8-methoxy-4-oxo-1,4-dihydroquinoline-3-carboxylic acid, and further preferably 7-[(3S,4S)-3-{(cyclopropy-lamino)methyl}-4-fluoropyrrolidine-1-yl]-6-fluoro-1-(2-fluoroethyl)-8-methoxy-4-oxo-1,4-dihydroquin oline-3-carboxylic acid.

The aqueous liquid formulation according to the present embodiment preferably contains a salt of the compound of the formula (1) from the viewpoint of the improvement of the solubility to water.

Examples of the salt of the compound of the formula (1) may include a salt formed with an inorganic acid such as hydrochloric acid, hydrobromic acid, sulfuric acid, and phosphoric acid, a salt formed with an organic acid such as maleic acid, fumaric acid, succinic acid, malic acid, malonic acid, methanesulfonic acid, toluenesulfonic acid, benzenesulfonic acid, lactic acid, oxalic acid, acetic acid, trifluoroacetic acid, and tartaric acid, and a salt formed with metal such as sodium, potassium, magnesium, calcium, aluminum, cesium, chromium, cobalt, copper, iron, zinc, platinum, and silver. Among these salts of the compound of the formula (1), a hydrochloride may be particularly preferable from the viewpoint of stability. In particular, a hydrochloride of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquin oline-3-carboxylic acid is excellent as a salt of the compound of the formula (1) contained in the aqueous liquid formulation according to the present embodiment, because decomposition by light exposure is unlikely to occur, and chemical decomposition is unlikely to occur even when the storage under accelerated test conditions is performed.

The concentration of the compound of the formula (1) in the liquid A is preferably 1.5 mg/mL or more, and more preferably 3.0 mg/mL or more, from the viewpoint of the inhibition of the chemical decomposition of the compound of the formula (1) or a salt thereof. The concentration may be furthermore preferably 3.5 mg/mL or more, still further more preferably 4.0 mg/mL or more, and particularly preferably 5.0 mg/mL or more.

On the other hand, the upper limit of the concentration of the compound of the formula (1) is preferably, but not particularly limited to, 8.0 mg/mL or less, from the viewpoint of the inhibition of the precipitation of the compound of the formula (1) or a salt thereof.

The above-described "concentration of the compound of the formula (1) in the liquid A" is a value obtained by dividing the weight (mg) of the compound of the formula (1) contained in the liquid A by the solvent amount (mL) of the liquid A. It is noted that when a salt of the compound of the formula (1) is used as a principal agent, the above-described "concentration of the compound of the formula (1) in the liquid A" is a value obtained by dividing the value (mg) of the weight of the compound of the formula (1) converted from the weight (mg) of the salt of the compound of the formula (1) contained in the liquid A, by the solvent amount (mL) of the liquid A.

In the present embodiment, the liquid B serves as the dilution liquid of the liquid A. The "dilution liquid" described herein is a solvent or solution used for diluting the liquid A, and represents any solvent or solution that is not harmful when administered to a patient. Examples of the solvent or solution which constitutes the liquid B may include water, a saline solution, a Ringer's solution, a glucose solution, a lactate Ringer's solution, an acetate Ringer's solution, a bicarbonate Ringer's solution, a maltose liquid, and a xylitol liquid. The liquid B may be, for example, one of these solvents or solutions, or a mixture of two or more of these solvents or solutions, and is preferably water.

In the present embodiment, the liquid B may contain a magnesium compound. When a magnesium compound is contained, the precipitation of the compound of the formula (1) or a salt thereof can be suppressed.

The "magnesium compound" described herein is a compound that contains magnesium. Examples of the magnesium compound may include an inorganic magnesium salt such as magnesium chloride, magnesium sulfate, magnesium nitrate, and magnesium phosphate, and an organic magnesium salt such as magnesium citrate, magnesium gluconate, magnesium acetate, and magnesium propionate. As the magnesium compound, one or more of these compounds may be used. The magnesium compound may preferably be an inorganic magnesium salt, and particularly preferably magnesium chloride.

It is noted that the liquid A preferably does not contain the magnesium compound, from the viewpoint of the solubility of the compound of the formula (1).

The use amount of the magnesium compound is, but not particularly limited to, preferably 0.35 or more, and further preferably 0.4 or more from the viewpoint of the molar ratio of the magnesium compound relative to the compound of the formula (1) or a salt thereof, from the viewpoint of the inhibition of the precipitation of the compound of the formula (1) or a salt thereof when the liquid A and the liquid B are mixed. The "molar ratio of the magnesium compound relative to the compound of the formula (1) or a salt thereof" is a value represented by the equation below:

"Molar ratio of magnesium compound relative to compound of formula (1) or salt thereof"=number of moles (mol) of magnesium compound contained in liquid B/number of moles (mol) of compound of formula (1) or salt thereof contained in liquid A.

Also, in consideration of the administration amount per day of the magnesium compound, the "molar ratio of magnesium compound relative to compound of formula (1) or a salt thereof" is preferably 3.0 or less, more preferably 1.5 or less, further preferably 1.0 or less, and particularly preferably 0.6 or less.

In the present embodiment, the liquid B may contain a buffer.

The "buffer" described herein has the action of maintaining the pH of a solution within a certain range, and is used for the purpose of stabilizing a formulation or reducing physiological stimuli. Examples thereof may include phosphoric acid, a phosphoric salt such as sodium dihydrogen phosphate, sodium monohydrogen phosphate, trisodium phosphate, sodium metaphosphate, potassium dihydrogen phosphate, potassium hydrogen phosphate (dipotassium phosphate), and tripotassium phosphate, citric acid such as citric acid or anhydrous citric acid, a citric salt such as calcium citrate hydrate, sodium citrate hydrate, disodium citrate, and anhydrous sodium citrate, ascorbic acid, magnesium L-aspartate, L-arginine, L-arginine hydrochloride, benzoic acid, sodium benzoate, epsilon-aminocaproic acid, ammonium chloride, potassium chloride, sodium chloride, glucosamine hydrochloride, triethanolamine hydrochloride, dried sodium sulfite, dried sodium carbonate, dilute hydrochloric acid, glycylglycine, glycine, calcium gluconate hydrate, L-glutamic acid, sodium L-glutamate, creatinine, chlorobutanol, disodium succinate hexahydrate, acetic acid, potassium acetate, sodium acetate hydrate, diethanolamine, tartaric acid, taurine, sodium hydrogen carbonate, sodium carbonate hydrate, triethanolamine, a triethanolamine sodium phosphate solution, trometamol (tris(hydroxymethyl)aminomethane), lactic acid, a sodium lactate solution, L-histidine, 4-(2-hydroxyethyl)-1-piperazineethanesulfonic acid, glacial acetic acid, glucose, benzalkonium chloride, boric acid, sodium borate, sodiumpolyphosphate, maleic acid, anhydrous sodium acetate, anhydrous sodium carbonate, meglumine, monoethanolamine, DL-malic acid, and rose oil. One or more of these buffers can be used. More preferably, sodium hydrogen carbonate, trometamol, a phosphoric salt, glycine, meglumine, citric acid, and a citric salt may be used. As a further preferable buffer, sodium hydrogen carbonate, trometamol, glycine, and meglumine are used, because high-pressure steam sterilization can be performed. Among these, sodium hydrogen carbonate, trometamol, and glycine may particularly preferably be used, because they are a safe buffer having low hemolysis.

The method for mixing the liquid A and the liquid B is not particularly limited, and can be appropriately defined by those skilled in the art. For example, the housing unit of the liquid A and the housing unit of the liquid B may be communicated with each other so that the liquid A and the liquid B are mixed.

Being "communicated with each other" described herein represents being joined to each other so that fluid can be distributed. When the housing unit of the liquid A and the housing unit of the liquid B are communicated with each other, both liquids are mixed in at least any one of the housing unit of the liquid A, the housing unit of the liquid B, and the region between the housing unit of the liquid A and the housing unit of the liquid B. The housing unit of the liquid A and the housing unit of the liquid B may be provided in one container, as a liquid A housing chamber and a liquid B housing chamber, respectively. Alternatively, the housing unit of the liquid A and the housing unit of the liquid B may be provided in separate containers (a liquid A housing container and a liquid B housing container) in the form of a kit product which is used such that the housing unit of the liquid A and the housing unit of the liquid B are communicated with each other when in use.

In the present embodiment, a pH adjuster may be used for adjusting the pH of the liquid A and the liquid B. The "pH adjuster" includes an acid, a base, or a buffer. Examples thereof may include hydrochloric acid, sulfuric acid, adipic acid or a salt thereof, citric acid or a salt thereof, gluconic acid or a salt thereof, succinic acid or a salt thereof, ascorbic acid or a salt thereof, glacial acetic acid or a salt thereof, acetic acid or a salt thereof, tartaric acid or a salt thereof, fumaric acid or a salt thereof, maleic acid or a salt thereof, lactic acid or a salt thereof, malic acid or a salt thereof, phosphoric acid or a salt thereof, glycine, sodium hydrogen carbonate, sodium carbonate, sodium hydroxide, and magnesium hydroxide. For example, one or more of these pH adjusters may be used. As the pH adjuster, hydrochloric acid and sodium hydroxide may be preferable, and hydrochloric acid and sodium hydroxide may be more preferable. With the pH adjuster, the pH of each of the liquid A and the liquid B can be adjusted within an appropriate range.

The pH of the liquid A is preferably 5.3 or less, more preferably 5.0 or less, further preferably 4.7 or less, particularly preferably 4.3 or less, and further preferably 3.3 or less, because the generation of the compound of the formula (2) can be suppressed. The lower limit of the pH of the liquid A is preferably 1.0 or more, because when the liquid A and the liquid B are mixed, a mixture having a near-neutral pH is obtained, and the precipitation of the compound of the formula (1) can be suppressed.

The pH of the liquid B is, but not particularly limited to, preferably 10.5 or less, and more preferably 10.0 or less, because when the magnesium compound is contained, the precipitation of the magnesium compound can be suppressed. The pH of the liquid B is preferably 7.0 or more, because when the liquid A and the liquid B are mixed, a mixture having a near-neutral pH is obtained, and the precipitation of the compound of the formula (1) can be suppressed. Also, when trometamol or glycine is used as the buffer, the pH is preferably 8.0 or more and 10.0 or less.

The pH of the mixture of the liquid A and the liquid B may be 6.3 or more, more preferably 6.3 or more and 7.1 or less, and particularly preferably 6.3 or more and 6.8 or less, because the precipitation of the compound of the formula (1) can be suppressed. The pH of the mixture of the liquid A and the liquid B can be adjusted within a preferable range by appropriately increasing or decreasing the added amount of the buffer to be used.

The content of the compound represented by the general formula (1) in the aqueous liquid formulation may be preferably 500 mg or less, further preferably 10 mg or more and 450 mg or less, more preferably 20 mg or more and 400 mg or less, further more preferably 30 mg or more and 200 mg or less, and particularly preferably 50 mg or more and 160 mg or less. The content of the compound represented by the general formula (1) when a salt of the compound represented by the general formula (1) is used represents a value (mg) obtained by converting the weight (mg) of the salt of the compound represented by the general formula (1) into the weight of the compound represented by the general formula (1).

(General Production Method)

The compound of the formula (1) or a salt thereof is dissolved or suspended in a physiologically acceptable carrier such as water, a saline solution, a Ringer's solution, a glucose solution, a lactate Ringer's solution, an acetate Ringer's solution, a bicarbonate Ringer's solution, a maltose liquid, and a xylitol liquid. The obtained solution or suspension may be further subjected to processes such as the process of adding a pH adjuster for adjusting a pH concentration and the process of adding a physiologically acceptable carrier for adjusting a final solution amount. By the above-described operation, there can be obtained the solution (liquid A) that contains the compound represented by the general formula (1) or a salt thereof and that has a pH of 5.3 or less.

Also, water, a saline solution, a Ringer's solution, a glucose solution, a lactate Ringer's solution, an acetate Ringer's solution, a bicarbonate Ringer's solution, a maltose liquid, a xylitol liquid, and the like can be used as the liquid B. For the preparation of the liquid B, a magnesium compound, a tonicity agent such as sodium chloride, and a buffer may be added to the solvent or solution which constitutes the liquid B. Furthermore, the pH may be adjusted by the process of adding a pH adjuster. Furthermore, the solution amount may be adjusted by the process of adding a physiologically acceptable carrier to the solvent or solution which constitutes the liquid B.

By the above-described operation, there can be obtained the liquid B that can be used for diluting the liquid A.

EXAMPLES

Although the present invention will be described in further detail with reference to examples below, these examples do not limit the scope of the present invention.

In Examples below, the NMR spectrum was measured using a JNM-EX400 type nuclear magnetic resonance apparatus manufactured by JEOL Ltd. with tetramethyl silane (TMS) as an internal standard. The MS spectrum was measured using JMS-T100LP type and JMS-SX102A type mass spectrometers manufactured by JEOL Ltd. The elemental analysis was performed using a CHN CORDER MT-6 elemental analyzer manufactured by Yanaco Bunseki Co.

Also, powder X-ray diffraction was performed using RINT2200 manufactured by Rigaku Corporation. Copper radiation was used as radiation. The measurement condition was a tube current of 36 mA, a tube voltage of 40 kV, a divergence slit of 1 degree, a scattering slit of 1 degree, a

Reference Example 1

Bis(acetato-O)-{6,7-difluoro-1-(2-fluoroethyl)-8-methoxy-4-oxo-1,4-dihydroquinoline-3-carboxylato-$O^3,O^4$}boron Under nitrogen atmosphere, 103 g (1.67 mol) of boric acid (for the formation of a catalyst) was added to 21.4 L (225 mol) of anhydrous acetic acid.

The mixture was heated and stirred at 70.0 to 76.9° C. for 30 minutes (stirring speed: 69.5 rpm). The product was cooled to an internal temperature of 24.6° C. Thereafter, 1.01 kg (16.3 mol) of boric acid (first portion) was added, and the mixture was stirred at 24.6 to 27.4° C. for 30 minutes. Then, 1.01 kg (16.3 mol) of boric acid (second portion) was added, and the mixture was stirred at 24.7 to 27.5° C. for 30 minutes. Next, 1.01 kg (16.3 mol) of boric acid (third portion) was added, and the mixture was stirred at 24.7 to 27.7° C. for 30 minutes. Subsequently, 1.01 kg (16.3 mol) of boric acid (forth portion) was added, and the mixture was stirred at 25.4 to 29.4° C. for 30 minutes. Furthermore, the resultant product was stirred at 50.0 to 56.9° C. for 30 minutes to obtain a boric acid triacetate adjusting liquid. To the adjusting liquid, 5.50 kg (16.7 mol) of 6,7-difluoro-1-(2-fluoroethyl)-8-methoxy-4-oxo-1,4-dihydroquin oline-3-carboxylic acid ethyl ester was added, and the adjusting liquid was stirred at 54.7 to 56.9° C. for 3 hours. The product was cooled to 30.0° C., and allowed to stand at room temperature overnight. The resultant product was heated to 58.6° C. for dissolution. Then, 16.5 L of acetone was added to the adjusting liquid to obtain a reaction liquid (1).

Under nitrogen atmosphere, a mixture of 193 L of water and 33.7 L (555 mol) of aqueous ammonia (28%) was cooled to −0.6° C. To the cooled mixture, the aforementioned reaction liquid (1) was added, and the vessel for reaction liquid (1) was washed with 11.0 L of acetone. Thus, the reaction liquid (2) was obtained. The reaction liquid (2) was cooled to 15.0° C., and thereafter stirred at 4.3 to 15.0° C. for one hour. Precipitated crystals were separated by filtration, and washed with 55.0 L of water. Thus, 14.1 kg of wet crude crystals were obtained. The obtained crystals were dried under reduced pressure at a preset temperature of 65.0° C. for approximately 22 hours to obtain 6.93 kg of crude crystals (yield: 96.7%).

To the obtained crude crystals, 34.7 L of acetone was added under nitrogen atmosphere, and the obtained liquid was heated (hot water preset temperature: 57.0° C.) to dissolve the crude crystal. During the heating, 69.3 L of diisopropyl ether was dropped until crystallization occurred (dropping amount: 12.0 L). After crystallization was confirmed, the solution was stirred at 48.3 to 51.7° C. for 15 minutes. Then, the remaining diisopropyl ether was dropped, and stirred at 45.8 to 49.7° C. for 15 minutes. The solution was cooled to 15° C., and thereafter stirred at 6.5 to 15.0° C. for 30 minutes. The precipitated crystals were separated by filtration, and washed with 6.93 L of acetone and 13.9 L of diisopropyl ether. Thus, 7.41 kg of wet crystals were obtained. The obtained wet crystals were dried under reduced pressure at a preset temperature of 65.0° C. for approximately 20 hours to obtain 6.47 kg of bis(acetato-O)-{6,7-difluoro-1-(2-fluoroethyl)-8-methoxy-4-oxo-1,4-dihy-droquinoline-3-carboxylato-$O^3,O^4$}boron (yield: 90.3%). Elemental Analysis Value (%): as $C_{17}H_{15}BF_3NO_8$ Calcd.: C, 47.58; H, 3.52; N, 3.26.
Measured: C, 47.41; H, 3.41; N, 3.20.
$^1$H-NMR (CDCl$_3$, 400 MHz) δ: 2.04 (6H, s), 4.21 (3H, d, J=2.9 Hz), 4.88 (2H, dt, J=47.0, 4.4 Hz), 5.21 (2H, dt, J=24.9, 3.9 Hz), 8.17 (1H, t, J=8.8 Hz), 9.10 (1H, s).
ESI MS (positive) m/z: 430 (M+H)$^+$.

Reference Example 2

7-[(3S,4S)-3-{(cyclopropylamino)methyl}-4-fluoro-pyrrolidine-1-yl]-6-fluoro-1-(2-fluoroethyl)-8-methoxy-4-oxo-1,4-dihydroquinoline-3-carboxylic acid hydrochloride Under nitrogen atmosphere, a mixed liquid of 3.56 kg (15.4 mol) of (3R,4S)-3-cyclopropylaminomethyl-4-fluoro-pyrrolidine, 11.7 L (84.2 mol) of triethylamine, and 30.0 L of dimethyl sulfoxide was stirred at 23.0 to 26.3° C. for 15 minutes. At 23.0 to 26.3° C., 6.00 kg (14.0 mol) of bis (acetato-O){6,7-difluoro-1-(2-fluoroethyl)-8-methoxy-4-oxo-1,4-dihydroquinoline-3-carboxylato-$O^3,O^4$}boron was added. The mixture was stirred at 23.7 to 26.3° C. for 2 hours. To the reaction liquid, 120 L of ethyl acetate was added, and 120 L of water was further added. Thereafter, a solution of 960 g (an amount for obtaining 2 mol/L) of sodium hydroxide and 12.0 L of water was added. After the mixture was stirred for 5 minutes, an aqueous layer was separated. To the aqueous layer, 120 L of ethyl acetate was added. The mixture was stirred for 5 minutes. Then, an ethyl acetate layer was separated. The portions of the ethyl acetate layer were combined, and 120 L of water was added. The mixture was stirred for 5 minutes, and left to stand. Then, an aqueous layer was removed. The ethyl acetate layer was evaporated under reduced pressure. The obtained residue was dissolved in 60.0 L of 2-propanol, and the solution was allowed to stand at room temperature overnight. A solution of 5.24 L (62.9 mol) of hydrochloric acid and 26.2 L (an amount for obtaining 2 mol/L) of water was added. The mixture was stirred at 28.2 to 30.0° C. for 30 minutes, and heated at an outer temperature of 55.0° C. After dissolution (dissolution was confirmed at 47.1°), the mixed liquid was cooled, resulting in crystallization. The mixed liquid was stirred at 39.9 to 41.0° C. for 30 minutes. After cooling (approximately temperature setting: 7.0° C. untill 20° C. and −10.0° C. below 20.0° C.), the resultant product was stirred at 2.2 to 10.0° C. for one hour. Precipitated crystals were collected by filtration, and washed with 60 L of 2-propanol to obtain 9.57 kg of wet crude crystals of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquin oline-3-carboxylic acid hydrochloride.

Reference Example 3

A-type Crystals of 7-[(3S,4S)-3-{(cyclopropy-lamino)methyl}-4-fluoropyrrolidine-1-yl]-6-fluoro-1-(2-fluoroethyl)-8-methoxy-4-oxo-1,4-dihydroqui-noline-3-carboxylic acid hydrochloride (Compound (1))

To a mixed liquid of 60 L of ethanol and 10.8 L of purified water, 9.57 kg of wet crude crystals of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquin oline-3-carboxylic acid hydrochloride was added, and dissolved by heating. This solution was filtered, and the vessel for the solution was washed with a mixed liquid of 24.0 L of ethanol and 1.20 L of purified water. The dissolution was confirmed, and 96.0 L of heated ethanol (99.5) was added at 71.2 to 72.6° C. This solution was cooled (hot water preset temperature: 60.0° C.), and crystallization was confirmed (crystallization temperature: 61.5° C.). Thereafter, the obtained product was stirred at 59.4 to 61.5° C. for 30 minutes, and cooled in a stepwise manner (Hot water temperature setting: 40° C. until 50° C., 30° C. until 40° C., 20° C. until 30° C., 7.0° C. until 20.0° C., −10° C. until 15.0° C., and then left to stand), and stirred at 4.8 to 10.0° C. for one hour. Precipitated crystals were separated by filtration, and washed with 30.0 L of ethanol to obtain 5.25 kg of wet crystals of 7-[(3S,4S)-3-{(cyclopropylamino)methyl}-4-fluoropyrrolidine-1-yl]-6-fluoro-1-(2-fluoroethyl)-8-methoxy-4-oxo-1,4-dihydroquin oline-3-carboxylic acid hydrochloride. The obtained crystals were dried under reduced pressure at a preset temperature of 50.0° C. for approximately 13 hours to obtain 4.83 kg of the compound (1) (yield: 72.6%).

Figure 1:
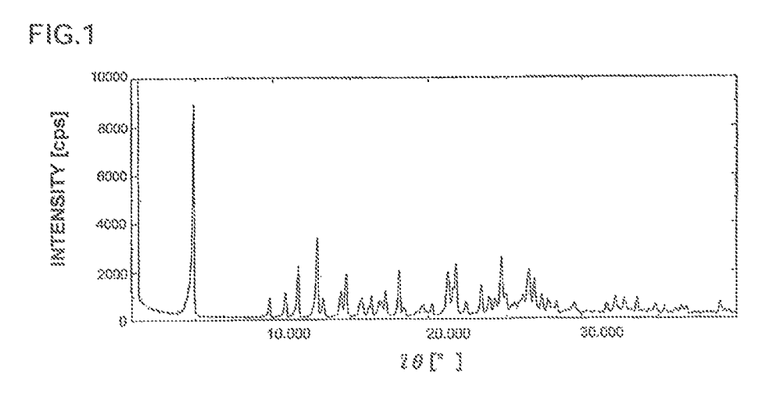
FIG. 1 illustrates a powder X-ray diffraction pattern of A-type crystals of 7-[(3S,4S)-3-{(cyclopropylamino) methyl}-4-fluoropyrrolidine-1-yl]-6-fluoro-1-(2-fluoro-ethyl)-8-methoxy-4-oxo-1,4-dihydroquin oline-3-carboxylic acid hydrochloride.
Figure 2:
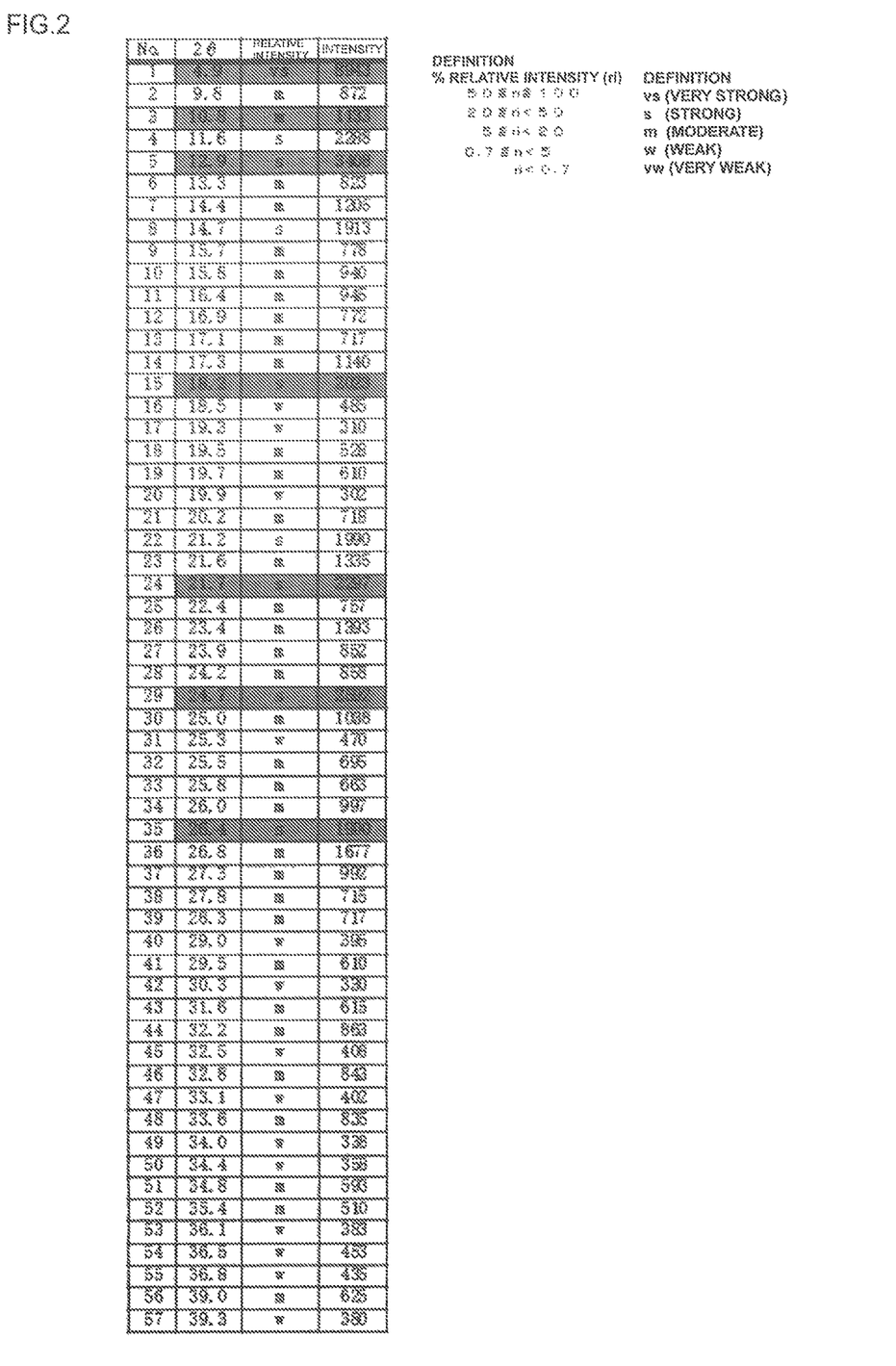
FIG. 2 is a table describing peaks having a relative intensity of 0.7 or more when the intensity of the peak at 2θ=4.9 degrees in the diffraction pattern illustrated in FIG. 1 is assumed to be 100.

The result of the powder X-ray diffraction of the compound (1) based on WO2013/069297 is shown in FIGS. 1 and 2. As understood from FIGS. 1 and 2, peaks are observed at 4.9 degrees, 9.8 degrees, 10.8 degrees, 12.9 degrees, 14.7 degrees, 18.2 degrees, 21.7 degrees, 23.4 degrees, 24.7 degrees, and 26.4 degrees, and characteristic peaks can be confirmed at 4.9 degrees, 10.8 degrees, 12.9 degrees, 18.2 degrees, 21.7 degrees, 24.7 degrees and 26.4 degrees. Particularly characteristic peaks can be confirmed at 10.8 degrees, 12.9 degrees, and 24.7 degrees.

Elemental Analysis Value (%): as $C_{21}H_{24}F_3N_3O_4HCl$
Calcd.: C, 53.00; H, 5.30; N, 8.83.
Measured: C, 53.04; H, 5.18; N, 8.83.
$^1$H NMR (DMSO-d6, 400 MHz) δ (ppm): 0.77-0.81 (2H, m), 0.95-1.06 (2H, m), 2.80-2.90 (2H, m), 3.21-3.24 (1H, m), 3.35-3.39 (1H, m), 3.57 (3H, s), 3.65-3.78 (3H, m), 4.13 (1H, dd, J=41.8, 13.1 Hz), 4.64-4.97 (3H, m), 5.14 (1H, dd, J=32.7, 15.6 Hz), 5.50 (1H, d, J=53.7 Hz), 7.80 (1H, d, J=13.7 Hz), 8.86 (1H, s), 9.44 (2H, brs), 15.11 (1H, brs).
ESI MS (positive) m/z: 440 (M+H)$^+$.
(pH of Liquid A)

Example 1

In water for injection, 433.2 mg of the compound (1) was dissolved. To the obtained solution, 0.1 mol/L hydrochloric acid was added to adjust the pH to 2.0. To this solution, water for injection was added so that the total amount became 60 mL. Thus, the liquid A was prepared.

It is noted that as water for injection, the water for injection defined in the Japanese Pharmacopoeia 16th Edition was used (the same applies hereinafter).

Example 2

In water for injection, 433.2 mg of the compound (1) was dissolved. To the obtained solution, 0.1 mol/L hydrochloric acid was added to adjust the pH to 2.5. To this solution, water for injection was added so that the total amount became 60 mL. Thus, the liquid A was prepared.

Example 3

In water for injection, 433.2 mg of the compound (1) was dissolved. To the obtained solution, 0.1 mol/L hydrochloric acid was added to adjust the pH to 3.0. To this solution, water for injection was added so that the total amount became 60 mL. Thus, the liquid A was prepared.

Example 4

In water for injection, 433.2 mg of the compound (1) was dissolved. To the obtained solution, 0.1 mol/L hydrochloric acid was added to adjust the pH to 3.5. To this solution, water for injection was added so that the total amount became 60 mL. Thus, the liquid A was prepared.

Example 5

In water for injection, 433.2 mg of the compound (1) was dissolved. To the obtained solution, 0.1 mol/L hydrochloric acid was added to adjust the pH to 4.0. To this solution, water for injection was added so that the total amount became 60 mL. Thus, the liquid A was prepared.

Example 6

In water for injection, 433.2 mg of the compound (1) was dissolved. To the obtained solution, 0.1 mol/L hydrochloric acid was added to adjust the pH to 4.5. To this solution, water for injection was added so that the total amount became 60 mL. Thus, the liquid A was prepared.

Example 7

In water for injection, 433.2 mg of the compound (1) was dissolved. To the obtained solution, 0.1 mol/L hydrochloric acid was added to adjust the pH to 5.0. To this solution, water for injection was added so that the total amount became 60 mL. Thus, the liquid A was prepared.

Comparative Example 1

In water for injection, 433.2 mg of the compound (1) was dissolved. To the obtained solution, 0.1 mol/L hydrochloric acid was added to adjust the pH to 5.5. To this solution, water for injection was added so that the total amount became 60 mL. Thus, the liquid A was prepared.

Test Example 1

The liquid A prepared in each of Examples 1 to 7 and Comparative Example 1 was stored in a constant-temperature bath at 60±2° C. for 4 weeks. Then, the content of 7-{(3S,4S)-3-aminomethyl-4-fluoropyrrolidine-1-yl}-6-fluoro-1-(2-fluoroethyl)-8-methoxy-4-oxo-1,4-dihydroquinoline-3-carboxylic acid (the compound (2)) and the content of the compound (1) were measured by liquid chromatography (Alliance system, manufactured by Waters company).

pH measurement method: measured in accordance with the pH measurement method defined in General Test Methods of the Japanese Pharmacopoeia (the same applies in the following Test Examples).

(Condition of Measurement by Liquid Chromatography)

Separation column: a stainless tube having an inner diameter of 4.6 mm and a length of 15 cm was filled with octadecyl silylated silica gel for liquid chromatography with the size of 3 μm.

Liquid C: a 1000 mL solution obtained by dissolving 2.16 g of sodium 1-octanesulfonate in diluted phosphoric acid (1→1000)

Liquid D: methanol for liquid chromatography

Flow velocity: 1.0 mL

Detector: UV absorptiometer (measurement wavelength: 294 nm)
Retention time: relative retention time of compound (2) to compound (1): 0.69
Liquid sending: the mixing ratio of liquid C and liquid D is indicated in Table 1.

TABLE 1

Mixing ratio of liquid C and liquid D

| Analysis time (minute) | Liquid C | Liquid D |
|---|---|---|
| 0~32 | 56 | 44 |
| 32~50 | 56→30 | 44→70 |
| 50~60 | 30 | 70 |

Figure 3:
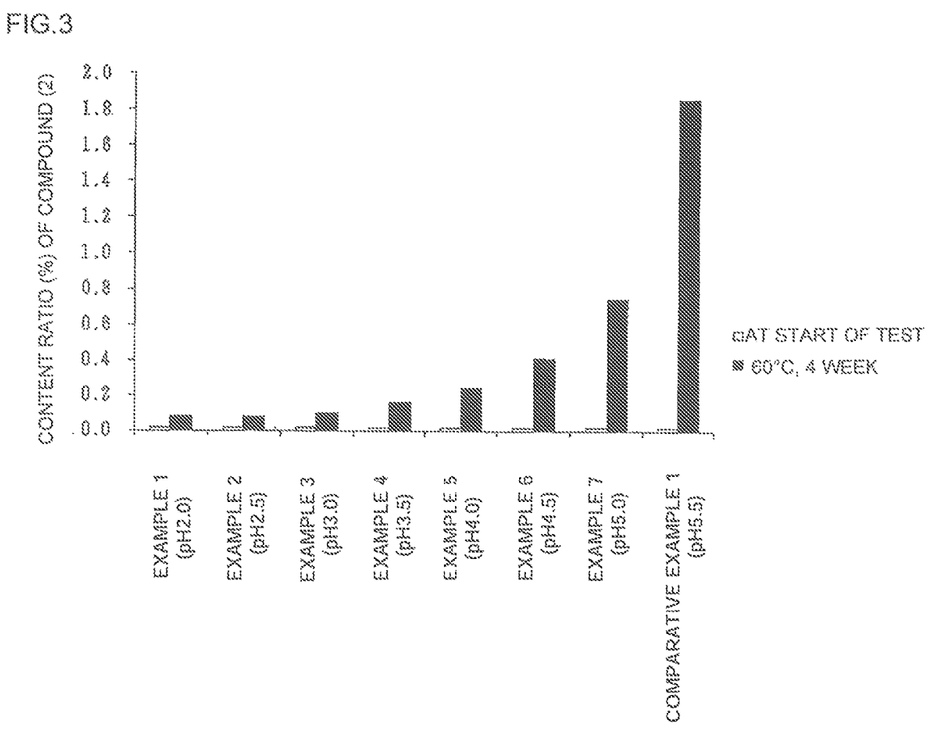
FIG. 3 is a graph illustrating the content ratio of the compound (2) in Examples 1 to 7 and Comparative Example 1, in terms of the percentage of the content of the compound (2) relative to the content of the compound (1).

The content ratio of the compound (2) is shown in FIG. 3 as the percentage of the content of the compound (2) relative to the content of the compound (1). As apparent from the result in FIG. 3, when the pH of the liquid A became higher, the content ratio of the compound (2) after the storage at 60° C. for 4 weeks increased. When the pH became as high as 5.5 (Comparative Example 1), the content ratio of the compound (2) became twice or more compared to the content ratio when the pH was 5.0 (Example 7). On the other hand, when the pH was adjusted to 5.3 or less (Examples 1 to 7), the inhibition of the generation of the compound (2) was achieved. As the pH became lower, the content ratio of the compound (2) decreased. In particular, at a pH of 3.0 or less (Examples 1 to 3), even when the storage at 60° C. for 4 weeks was performed, the content of the compound (2) tended to be unlikely to increase compared to that at the start of test.

pH of Liquid B

Reference Example 4

In water for injection, 92 g of magnesium chloride was dissolved. With a 0.1 mol/L sodium hydroxide solution and water for injection, the liquid B having a pH of 9.9 (100 mL) was prepared.

Reference Example 5

In water for injection, 92 g of magnesium chloride was dissolved. With a 0.1 mol/L sodium hydroxide solution and water for injection, the liquid B having a pH of 10.5 (100 mL) was prepared.

Reference Example 6

In water for injection, 92 g of magnesium chloride was dissolved. With a 0.1 mol/L sodium hydroxide solution and water for injection, the liquid B having a pH of 10.6 (100 mL) was prepared.

Test Example 2

The liquid B according to each of Reference Examples 4 to 6 was measured for the pH and visually observed for appearance.
Observation method: observed using a foreign substance checker (illuminance: 1000 to 2000 lx) (the same applies in the following Test Examples).

TABLE 2 pH and visual observation result of liquid B

| | pH | Appearance |
|---|---|---|
| Reference Example 4 | 9.9 | Colorless, clear liquid |
| Reference Example 5 | 10.5 | Colorless, clear liquid |
| Reference Example 6 | 10.6 | White precipitate observed |

As apparent from the test result indicated in Table 2, a white precipitate was observed in Reference Example 6 having a pH of 10.6. However, in Reference Examples 4 and 5 having a pH of 10.5 or less, a precipitate was not precipitated, and a colorless, clear liquid was obtained.

pH of Mixed Liquid of Liquid A and Liquid B

Example 8

According to the formulation indicated in Table 3, 433.2 mg of the compound (1) was dissolved in water for injection. To the solution, 0.1 mol/L hydrochloric acid or a 0.1 mol/L sodium hydroxide solution was added to adjust the pH to 4.0. To this solution, water for injection was added so that the total amount became 100 mL. Thus, the liquid A was obtained. Also, 92 mg of magnesium chloride, 100 mg of potassium dihydrogen phosphate, 200 mg of disodium hydrogen phosphate anhydrous, and 1586 mg of sodium chloride were dissolved in water for injection. To the solution, 0.1 mol/L hydrochloric acid or a 0.1 mol/L sodium hydroxide solution was added to adjust the pH to 7.6. To this solution, water for injection was added so that the total amount became 100 mL. Thus, the liquid B was obtained. The whole quantities of the liquid A and the liquid B were mixed to obtain an injectable formulation.

Example 9

According to the formulation indicated in Table 3, 433.2 mg of the compound (1) was dissolved in water for injection. To the solution, 0.1 mol/L hydrochloric acid or a 0.1 mol/L sodium hydroxide solution was added to adjust the pH to 4.0. To this solution, water for injection was added so that the total amount became 100 mL. Thus, the liquid A was obtained. Also, 92 mg of magnesium chloride, 100 mg of potassium dihydrogen phosphate, 200 mg of disodium hydrogen phosphate anhydrous, and 1586 mg of sodium chloride were dissolved in water for injection. To the solution, 0.1 mol/L hydrochloric acid or a 0.1 mol/L sodium hydroxide solution was added to adjust the pH to 7.2. To this solution, water for injection was added so that the total amount became 100 mL. Thus, the liquid B was obtained. The whole quantities of the liquid A and the liquid B were mixed to obtain an injectable formulation.

Example 10

According to the formulation indicated in Table 3, 433.2 mg of the compound (1) was dissolved in water for injection. To the solution, 0.1 mol/L hydrochloric acid or a 0.1 mol/L sodium hydroxide solution was added to adjust the pH to 4.0. To this solution, water for injection was added so that the total amount became 100 mL. Thus, the liquid A was obtained. Also, 92 mg of magnesium chloride, 100 mg of potassium dihydrogen phosphate, 200 mg of disodium hydrogen phosphate anhydrous, and 1586 mg of sodium chloride were dissolved in water for injection. To the solution, 0.1 mol/L hydrochloric acid or a 0.1 mol/L sodium hydroxide solution was added to adjust the pH to 6.8. To this solution, water for injection was added so that the total amount became 100 mL. Thus, the liquid B was obtained. The whole quantities of the liquid A and the liquid B were mixed to obtain an injectable formulation.

Example 11

According to the formulation indicated in Table 3, 433.2 mg of the compound (1) was dissolved in water for injection. To the solution, 0.1 mol/L hydrochloric acid or a 0.1 mol/L sodium hydroxide solution was added to adjust the pH to 4.0. To this solution, water for injection was added so that the total amount became 100 mL. Thus, the liquid A was obtained. Also, 92 mg of magnesium chloride, 100 mg of potassium dihydrogen phosphate, 200 mg of disodium hydrogen phosphate anhydrous, and 1586 mg of sodium chloride were dissolved in water for injection. To the solution, 0.1 mol/L hydrochloric acid or a 0.1 mol/L sodium hydroxide solution was added to adjust the pH to 6.6. To this solution, water for injection was added so that the total amount became 100 mL. Thus, the liquid B was obtained. The whole quantities of the liquid A and the liquid B were mixed to obtain an injectable formulation.

TABLE 3

Prescription

| | Components | Example 8 | Example 9 | Example 10 | Example 11 |
|---|---|---|---|---|---|
| Liquid A | Compound (1) | 433.2 mg | 433.2 mg | 433.2 mg | 433.2 mg |
| | Hydrochloric acid | As needed | As needed | As needed | As needed |
| | Sodium hydroxide | As needed | As needed | As needed | As needed |
| | Water for injection | As needed | As needed | As needed | As needed |
| | (Total) | 100 mL | 100 mL | 100 mL | 100 mL |
| | (pH) | 4.0 | 4.0 | 4.0 | 4.0 |
| Liquid B | Magnesium chloride hexahydrate | 92 mg | 92 mg | 92 mg | 92 mg |
| | Potassium dihydrogen phosphate | 100 mg | 100 mg | 100 mg | 100 mg |
| | disodium hydrogen phosphate anhydrous | 200 mg | 200 mg | 200 mg | 200 mg |
| | Sodium chloride | 1586 mg | 1586 mg | 1586 mg | 1586 mg |
| | Hydrochloric acid | As needed | As needed | As needed | As needed |
| | Sodium hydroxide | As needed | As needed | As needed | As needed |
| | Water for injection | As needed | As needed | As needed | As needed |
| | (Total) | 100 mL | 100 mL | 100 mL | 100 mL |
| | (pH) | 7.6 | 7.2 | 6.8 | 6.6 |
| | (Total after mixing) | 200 mL | 200 mL | 200 mL | 200 mL |

Test Example 3

The injectable formulation according to each of Examples 8 to 11 was stored in a constant-temperature bath at 5±3° C. for one week. The resultant injectable formulation was measured for the pH and visually observed for appearance. The observation was performed before the storage (that is, immediately after the preparation; the same applies hereinafter) and after the storage of each injectable formulation at 5° C. for one week. The measurement of a pH and the observation for appearance were performed by the same methods as those in Test Example 2.

TABLE 4 pH and visual observation result of injectable formulation

| | pH | Before storage Appearance | After storage at 5° C. for 1 week Appearance |
|---|---|---|---|
| Example 8 | 6.6 | Slightly yellow, clear liquid | Slightly yellow, clear liquid |
| Example 9 | 6.5 | Slightly yellow, clear liquid | Slightly yellow, clear liquid |
| Example 10 | 6.3 | Slightly yellow, clear liquid | Slightly yellow, clear liquid |
| Example 11 | 6.2 | Slightly yellow, clear liquid | Crystals precipitated |

As apparent from the test result indicated in Table 4, in the injectable formulation according to Example 11 in which the mixed liquid had a pH of 6.2, crystals were precipitated after the storage at 5±3° C. for one week. On the other hand, in the injectable formulation according to each of Examples 8 to 10 in which the mixed liquid had a pH of 6.3 or more, the precipitation of crystals was not confirmed even after the storage at 5±3° C. for one week, and a slightly yellow, clear injectable formulation was obtained.

Formulation Examples

Example 12

According to the formulation indicated in Table 5, 433.2 mg of the compound (1) was dissolved in water for injection. To the solution, 0.1 mol/L hydrochloric acid or a 0.1 mol/L sodium hydroxide solution was added to adjust the pH to 3.0. To this solution, water for injection was added so that the total amount became 60 mL. Thus, the liquid A was obtained. Also, 92 mg of magnesium chloride, 120 mg of trometamol, and 1700 mg of sodium chloride were dissolved in water for injection. With 0.1 mol/L hydrochloric acid or a 0.1 mol/L sodium hydroxide solution, and water for injection, the liquid B (140 mL) having a pH of 9.2 was prepared. The whole quantities of the liquid A and the liquid B were mixed to obtain an injectable formulation.

Example 13

According to the formulation indicated in Table 5, 433.2 mg of the compound (1) was dissolved in water for injection.

To the solution, 0.1 mol/L hydrochloric acid or a 0.1 mol/L sodium hydroxide solution was added to adjust the pH to 3.0. To this solution, water for injection was added so that the total amount became 60 mL. Thus, the liquid A was obtained. Also, 92 mg of magnesium chloride, 200 mg of sodium hydrogen carbonate, and 1630 mg of sodium chloride were dissolved in water for injection. With 0.1 mol/L hydrochloric acid or a 0.1 mol/L sodium hydroxide solution, and water for injection, the liquid B (140 mL) having a pH of 8.0 was prepared. The whole quantities of the liquid A and the liquid B were mixed to obtain an injectable formulation.

TABLE 5

Prescription

| | Components | Example 12 | Example 13 |
|---|---|---|---|
| Liquid A | Compound (1) | 433.2 mg | 433.2 mg |
| | Hydrochloric acid | As needed | As needed |
| | Sodium hydroxide | As needed | As needed |
| | Water for injection | As needed | As needed |
| | (Total) | 60 mL | 60 mL |
| Liquid B | Magnesium chloride hexahydrate | 92 mg | 92 mg |
| | Trometamol | 120 mg | — |
| | Sodium hydrogen carbonate | — | 200 mg |
| | Sodium chloride | 1700 mg | 1630 mg |
| | Hydrochloric acid | As needed | As needed |
| | Sodium hydroxide | As needed | As needed |
| | Water for injection | As needed | As needed |
| | (Total) | 140 mL | 140 mL |
| (Total after mixing) | | 200 mL | 200 mL |

Test Example 4

The injectable formulation according to each of Example 12 and Example 13 was measured for the pH and visually observed for appearance. The measurement of a pH and the observation for appearance were performed by the same methods as those in Test Example 2.

TABLE 6

Preparation result

| | Liquid A | | Liquid B | | Mixed liquid | |
|---|---|---|---|---|---|---|
| | pH | Appearance | pH | Appearance | pH | Appearance |
| Example 12 | 3.0 | Pale yellow, clear liquid | 9.2 | Colorless, clear liquid | 6.5 | Slightly yellow, clear liquid |
| Example 13 | 3.0 | Pale yellow, clear liquid | 8.0 | Colorless, clear liquid | 6.5 | Slightly yellow, clear liquid |

As apparent from the test result indicated in Table 6, when the pH of the liquid B was 9.2 in the case of trometamol (Example 12), and 8.0 in the case of sodium hydrogen carbonate (Example 13), the pH of the mixed liquid could be adjusted to approximately 6.5, and a clear injection liquid without a precipitate could be prepared.

Example 14

According to the formulation indicated in Table 7, 81.23 mg of the compound (1) was dissolved in water for injection. To the solution, 0.1 mol/L hydrochloric acid or a 0.1 mol/L sodium hydroxide solution was added to adjust the pH to 3.0. To this solution, water for injection was added so that the total amount became 12 mL. Thus, the liquid A was obtained. Also, 17.4 mg of magnesium chloride, 30 mg of trometamol, and 530 mg of sodium chloride were dissolved in water for injection. With 0.1 mol/L hydrochloric acid or a 0.1 mol/L sodium hydroxide solution, and water for injection, the liquid B (50 mL) having a pH of 8.8 was prepared. The whole quantities of the liquid A and the liquid B were mixed to obtain an injectable formulation.

Example 15

According to the formulation indicated in Table 7, 81.23 mg of the compound (1) was dissolved in water for injection. To the solution, 0.1 mol/L hydrochloric acid or a 0.1 mol/L sodium hydroxide solution was added to adjust the pH to 3.0. To this solution, water for injection was added so that the total amount became 12 mL. Thus, the liquid A was obtained. Also, 17.4 mg of magnesium chloride, 25 mg of glycine, and 560 mg of sodium chloride were dissolved in water for injection. With 0.1 mol/L hydrochloric acid or a 0.1 mol/L sodium hydroxide solution, and water for injection, the liquid B (50 mL) having a pH of 9.6 was prepared. The whole quantities of the liquid A and the liquid B were mixed to obtain an injectable formulation.

Example 16

According to the formulation indicated in Table 7, 162.5 mg of the compound (1) was dissolved in water for injection. To the solution, 0.1 mol/L hydrochloric acid or a 0.1 mol/L sodium hydroxide solution was added to adjust the pH to 3.0. To this solution, water for injection was added so that the total amount became 24 mL. Thus, the liquid A was obtained. Also, 34.7 mg of magnesium chloride, 60 mg of trometamol, and 860 mg of sodium chloride were dissolved in water for injection. With 0.1 mol/L hydrochloric acid or a 0.1 mol/L sodium hydroxide solution, and water for injection, the liquid B (76 mL) having a pH of 8.8 was prepared. The whole quantities of the liquid A and the liquid B were mixed to obtain an injectable formulation.

Example 17

According to the formulation indicated in Table 7, 162.5 mg of the compound (1) was dissolved in water for injection. To the solution, 0.1 mol/L hydrochloric acid or a 0.1 mol/L sodium hydroxide solution was added to adjust the pH to 3.0. To this solution, water for injection was added so that the total amount became 24 mL. Thus, the liquid A was obtained. Also, 34.7 mg of magnesium chloride, 75 mg of glycine, and 840 mg of sodium chloride were dissolved in water for injection. With 0.1 mol/L hydrochloric acid or a 0.1 mol/L sodium hydroxide solution, and water for injection, the liquid B (76 mL) having a pH of 9.3 was prepared. The whole quantities of the liquid A and the liquid B were mixed to obtain an injectable formulation.

TABLE 7

| | | Prescription | | | |
|---|---|---|---|---|---|
| | Components | Example 14 | Example 15 | Example 16 | Example 17 |
| Liquid A | Compound (1) | 81.23 mg | 81.23 mg | 162.5 mg | 162.5 mg |
| | Hydrochloric acid | As needed | As needed | As needed | As needed |
| | Sodium hydroxide | As needed | As needed | As needed | As needed |
| | Water for injection | As needed | As needed | As needed | As needed |
| | (Total) | 12 mL | 12 mL | 24 mL | 24 mL |
| | (pH) | 3.0 | 3.0 | 3.0 | 3.0 |
| Liquid B | Magnesium chloride hexahydrate | 17.4 mg | 17.4 mg | 34.7 mg | 34.7 mg |
| | Trometamol | 30 mg | — | 60 mg | — |
| | Glycine | — | 25 mg | — | 75 mg |
| | Sodium chloride | 530 mg | 560 mg | 860 mg | 840 mg |
| | Hydrochloric acid | As needed | As needed | As needed | As needed |
| | Sodium hydroxide | As needed | As needed | As needed | As needed |
| | Water for injection | As needed | As needed | As needed | As needed |
| | (Total) | 50 mL | 50 mL | 76 mL | 76 mL |
| | (pH) | 8.8 | 9.6 | 8.8 | 9.3 |
| | (Total after mixing) | 62 mL | 62 mL | 100 mL | 100 mL |

Test Example 5

The injectable formulation according to each of Examples 14 to 17 was measured for the pH and visually observed for appearance. The measurement of a pH and the observation for appearance were performed by the same methods as those in Test Example 2.

TABLE 8

| | Preparation result | | | | | |
|---|---|---|---|---|---|---|
| | Liquid A | | Liquid B | | Mixed liquid | |
| | pH | Appearance | pH | Appearance | pH | Appearance |
| Example 14 | 3.0 | Pale yellow, clear liquid | 9.0 | Colorless, clear liquid | 6.6 | Slightly yellow, clear liquid |
| Example 15 | 3.0 | Pale yellow, clear liquid | 9.6 | Colorless, clear liquid | 6.6 | Slightly yellow, clear liquid |
| Example 16 | 3.0 | Pale yellow, clear liquid | 8.6 | Colorless, clear liquid | 6.6 | Slightly yellow, clear liquid |
| Example 17 | 3.0 | Pale yellow, clear liquid | 9.3 | Colorless, clear liquid | 6.4 | Slightly yellow, clear liquid |

As apparent from the test result indicated in Table 8, when the formulation of the liquid B was adjusted to the pH indicated in Table 8, the pH of the mixed liquid could be adjusted to approximately 6.5, and a clear injection liquid without a precipitate could be prepared.

INDUSTRIAL APPLICABILITY

An aqueous liquid formulation that contains a compound of formula (1) and that has an excellent antibacterial action against Gram-positive bacteria and Gram-negative bacteria is provided. The aqueous liquid formulation according to the present invention, in which the chemical decomposition of the compound of the formula (1) is suppressed, is industrially useful.

The invention claimed is:
1. An aqueous liquid formulation comprising:
liquid A: a solution comprising a compound represented by formula (1):

wherein $R^1$ represents an alkyl group having 1 to 3 carbon atoms which is optionally substituted with one or more substituents selected from the group consisting of a hydrogen atom, a halogen atom, an amino group, a cyano group, and a hydroxyl group, $R^2$ represents a hydrogen atom, a halogen atom, a hydroxyl group, an amino group or an alkyl group having 1 to 3 carbon atoms which is optionally substituted with one or more substituents selected from the group consisting of a hydrogen atom, a halogen atom, an amino group, a cyano group and a hydroxyl group, $R^3$ represents a hydrogen atom or a halogen atom, $R^4$ represents a hydrogen atom or a halogen atom, and X represents a halogen atom, or a salt thereof, and having a pH of 5.3 or less; and liquid B: a dilution liquid comprising a magnesium compound that is mixed with the liquid A to prepare a solution for administration, wherein a molar ratio of the magnesium compound relative to the compound represented by the formula (1) or salt thereof is 0.6 or less.

2. The aqueous liquid formulation according to claim 1, wherein the liquid A and the liquid B are mixed to prepare the solution for administration having a pH of 6.3 or more.

3. The aqueous liquid formulation according to claim 1, wherein the liquid A does not contain a magnesium compound.

4. The aqueous liquid formulation according to claim 1, wherein the liquid B further comprises a buffer.

5. The aqueous liquid formulation according to claim 4, wherein the buffer is selected from the group consisting of sodium hydrogen carbonate, trometamol, a phosphoric salt, glycine, meglumine, citric acid, and a citric salt.

6. The aqueous liquid formulation according to claim 4, wherein the buffer is selected from the group consisting of sodium hydrogen carbonate, trometamol, and glycine.

7. The aqueous liquid formulation according to claim 1, wherein a concentration of the compound represented by the formula (1) in the liquid A is 1.5 mg/mL or more and 8 mg/mL or less.

8. The aqueous liquid formulation according to claim 1, wherein the liquid A and the liquid B are housed in separate housing units, and are to be mixed by making the housing units of the liquid A and the liquid B communicate with each other when administered.

9. The aqueous liquid formulation according to claim 8, wherein the housing unit of the liquid A and the housing unit of the liquid B are constituted by separate containers, respectively.

10. An aqueous liquid formulation comprising:
liquid A: a solution comprising a compound represented by formula (1):

wherein $R^1$ represents an alkyl group having 1 to 3 carbon atoms which is optionally substituted with one or more substituents selected from the group consisting of a hydrogen atom, a halogen atom, an amino group, a cyano group, and a hydroxyl group, $R^2$ represents a hydrogen atom, a halogen atom, a hydroxyl group, an amino group or an alkyl group having 1 to 3 carbon atoms which is optionally substituted with one or more substituents selected from the group consisting of a hydrogen atom, a halogen atom, an amino group, a cyano group, and a hydroxyl group, $R^3$ represents a hydrogen atom or a halogen atom, $R^4$ represents a hydrogen atom or a halogen atom, and X represents a halogen atom, or a salt thereof, and having a pH of 5.3 or less, and liquid B: a solution comprising trometamol or glycine and a magnesium compound, and having a pH of 8.0 or more and 10.0 or less, wherein the liquid A and the liquid B are mixed to prepare a solution for administration.

* * * * *